United States Patent [19]
Knifton et al.

[11] Patent Number: 5,362,913
[45] Date of Patent: *Nov. 8, 1994

[54] SATURATED, AMINATED, ALKOXYLATED POLYBUTADIENES

[75] Inventors: John F. Knifton; Michael Cuscurida, both of Austin, Tex.

[73] Assignee: Huntsman Corporation, Salt Lake City, Utah

[*] Notice: The portion of the term of this patent subsequent to Feb. 19, 2006 has been disclaimed.

[21] Appl. No.: 976,914

[22] Filed: Nov. 16, 1992

[51] Int. Cl.$^5$ .............................. C07C 209/26
[52] U.S. Cl. .................. 564/480; 564/305; 564/504; 564/505
[58] Field of Search ............ 564/480, 504, 305, 505

[56] References Cited

U.S. PATENT DOCUMENTS

| | | | |
|---|---|---|---|
| 3,390,184 | 6/1968 | Moss et al. | 564/480 |
| 4,181,682 | 1/1980 | Watts, Jr. et al. | 564/480 |
| 4,658,062 | 4/1987 | Hinney et al. | 564/305 |
| 4,721,754 | 1/1988 | Baghdadchi | 525/194 |
| 4,812,524 | 3/1989 | Baghdadchi | 525/194 |
| 4,994,621 | 2/1991 | Yeakey et al. | 564/475 |
| 5,003,107 | 3/1991 | Zimmerman et al. | 564/480 |
| 5,068,444 | 11/1991 | Cuscurida et al. | 564/480 |

*Primary Examiner*—Richard L. Raymond
*Assistant Examiner*—Scott C. Rand
*Attorney, Agent, or Firm*—Russell R. Stolle; David L. Mossman

[57] ABSTRACT

Highly saturated, highly aminated alkoxylated polymers may be reliably made by an improved process involving the steps of (1) polymerizing one or more unsaturated hydrocarbons to form a liquid polymer, where at least one of the unsaturated hydrocarbons is butadiene; (2) providing the liquid polymer with terminal hydroxyl groups; (3) alkoxylating the hydroxylated liquid polymer with one or more alkylene oxides having at least three carbon atoms to provide secondary terminal hydroxyl groups; (4) simultaneously aminating and hydrogenating the alkoxylated liquid polymer to produce an essentially saturated, aminated, alkoxylated liquid polymer in the presence of hydrogen and ammonia and a catalyst. The catalyst preferably contains nickel as the single greatest component, with smaller amounts of copper, chromium and molybdenum. Excesses of hydrogen and ammonia are used in the final step.

13 Claims, No Drawings

SATURATED, AMINATED, ALKOXYLATED POLYBUTADIENES

FIELD OF THE INVENTION

The invention relates to polyoxyalkylene polyamines and, in one aspect, more particularly relates to saturated polyoxyalkylene polyamines made by simultaneously aminating and hydrogenating an alkoxylated, hydroxy-terminated polyalkene.

BACKGROUND OF THE INVENTION

Low molecular weight homo- and copolymers of 1,3-dienes have been known for a long time. It is advantageous for many uses to alter the properties of the hydrophobic polymers in a controlled fashion by the introduction of reactive groups, such as hydroxyl and amine groups. Typically, compounds terminated with these reactive groups may be used as curing agents for epoxy resins, as cross-linking agents or binders for textiles, and as intermediates in the preparation of polyureas, including flexible urethane foams and urethane elastomers. Likewise, polyoxyalkylene polyamines falling within the above description are well known.

For example, U.S. Pat. No. 4,658,062 relates to novel amine terminated polybutadiene compounds of the formula:

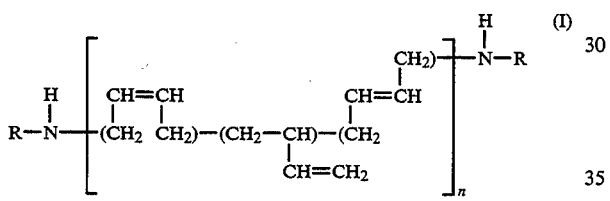

wherein R is hydrogen, a straight or branched chain alkyl group containing from 1 to 10 carbon atoms or a substituted or unsubstituted aryl or aralkyl group containing one or more benzenoid rings which may be fused or joined by single valency bonds, and n is an integer of from about 5 to about 1500 and a process for the preparation thereof. These materials are made by reacting an alkane or arenesulfonate terminated polybutadiene with a primary amine or ammonia. Further the process involves reacting a polyhydroxybutadiene homopolymer with an alkane or arenesulfonyl chloride or fluoride in the presence of a tertiary amine catalyst at a preferred temperature between 25° and 110° C. The process comprises a two-step procedure including an intermediate alkane or arenesulfonated polybutadiene.

There is described in U.S. Pat. No. 4,721,754 a polybutadiene composition useful for the preparation of polyurea and/or polyurethane elastomers comprising a blend of a polyhydroxybutadiene homopolymer and an amine-terminated polybutadiene. Similarly, U.S. Pat. No. 4,812,524 describes novel polyurea/polyurethane two-component adhesive compositions which comprise the reaction product of (a) a blend of an amine terminated polybutadiene and a polyhydroxybutadiene with (b) an aliphatic or aromatic di- or polyisocyanate and optionally chain extenders, tackifiers, coupling agents fillers and curingly effective amounts of catalysts.

There is U.S. Pat. No. 4,994,621 to Texaco Chemical Company, incorporated by reference herein. This patent teaches that aminated, alkoxylated hydroxyl-terminated polymers can be made by a process involving first polymerizing one or more unsaturated hydrocarbons, such as butadiene, to form a liquid polymer. Next, the liquid polymer is provided with terminal hydroxyl groups. Then, the hydroxylated liquid polymer is alkoxylated with one or more alkylene oxides, such as ethylene oxide, propylene oxide, butylene oxide and mixtures thereof, to provide second-ary terminal hydroxyl groups. Finally, the alkoxylated liquid polymer is aminated over a transition metal oxide catalyst, such as a combination of nickel oxide/copper oxide/chromium oxide. If the alkoxylated, hydroxyl-terminated liquid polymer is terminated with primary hydroxyl groups, then the amination does not proceed well. Although it is stated that "Typically, part or all of the double bonds are reduced in this amination procedure", the only structures of the aminated, alkoxylated hydroxyl-terminated polymers presented show the polybutadiene core to be unsaturated. Additionally, it was subsequently found that the end products of the process of this patent retained a relatively high degree of unsaturation.

Further, U.S. patent application Ser. No. 07/787,199, incorporated by reference herein, describes the synthesis of novel amine derivatives of hydroxyl-terminated polybutadienes having the formula:

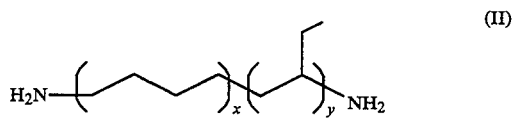

where x and y are integers, formed by amination and hydrogenation of a hydroxyl-terminated polybutadiene oligomer having an average molecular weight of 100 to 20,000 and a hydroxyl content of 0.1 to 20 meq/g in the presence of an inert solvent over a catalyst comprising Ni-Cu-Cr supported on alumina at a partial pressure of hydrogen sufficient to allow a flow rate of about 1 to 1000 scf $H_2$/lb hydroxyl-terminated polybutadiene (HTPB).

The term hydroxyl-terminated polybutadienes (HTPB) is used herein to include hydroxyl-terminated copolymers where at least one of the monomers used is butadiene. This definition includes hydroxyl-terminated homopolymers of butadiene.

It is always desirable to produce polyamines with improved properties for specific uses. It would be desirable to produce aliphatic amine derivatives of alkoxylated polybutadienes terminated with secondary hydroxyl groups which possessed a high concentration of secondary alkyl primary amines along with a high degree of saturation and a low equivalent weight of primary alkyl primary amines or secondary amines. Such compositions would be expected to be useful in RIM and polyurethane applications.

SUMMARY OF THE INVENTION

Accordingly, it is an object of the present invention to provide novel, saturated, aminated, alkoxylated polybutadienes.

It is another object of the present invention to provide a process for producing saturated, aminated, alkoxylated polybutadienes with a high degree of saturation and a high degree of amination.

In carrying out these and other objects of the invention, there is provided, in one form, a process for reliably making saturated, aminated alkoxylated polymers by the steps of: (1) polymerizing one or more unsaturated hydrocarbons to form a liquid polymer, where at least one of the unsaturated hydrocarbons is butadiene; (2) providing the liquid polymer with terminal hydroxyl groups; (3) alkoxylating the hydroxylated liquid polymer with one or more alkylene oxides having at least three carbon atoms to provide secondary terminal hydroxyl groups; (4) simultaneously aminating and hydrogenating the alkoxylated liquid polymer to produce an essentially saturated, aminated, alkoxylated liquid polymer in the presence of hydrogen and ammonia and a catalyst.

DETAILED DESCRIPTION OF THE INVENTION

It has been discovered that the preparation of primary amine terminated, saturated derivatives of alkoxylated polybutadienes having the general structure:

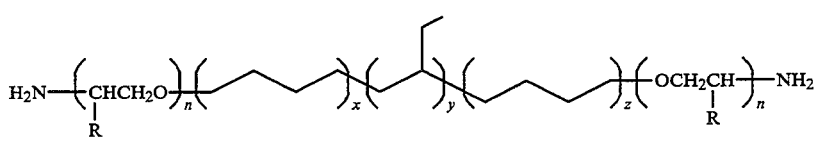
(III)

where x, y and z are integers, n independently ranges from 1 to about 100, R is an alkyl group having 1 to 4 carbon atoms and the number average molecular weight of the hydrocarbon backbone is 200–5000, may be achieved through a synthesis procedure where hydroxyl-terminated polybutadienes (HTPBs) are first alkoxylated in the presence of quaternary base catalysts and then selectively aminated and concurrently hydrogenated over a Ni—Cu—Cr—Mo on alumina catalyst. The concurrent or simultaneous amination/hydrogenation is achieved at initial hydrogen/NH$_3$/HTPB molar ratios of >50/>10/1. Preferentially, an inert solvent such as t-butanol is also present during the last step.

The reaction sequence may be briefly summarized, in a non-limiting example, by noting that a hydroxy terminated polybutadiene of the formula set out below:

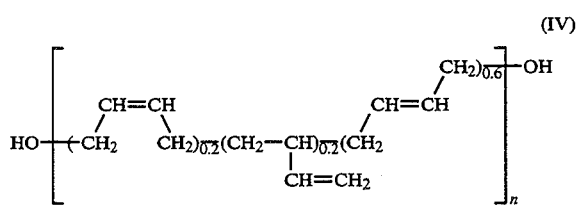
(IV)

where n ranges from about 10 to about 60, and the values 0.2 and 0.6 represent statistical distributions of isomer moieties by which butadiene can polymerize, is first alkoxylated and then simultaneously hydrogenated and aminated. It was discovered that the reaction intermediate is, in one aspect, preferably capped with an alkylene oxide having at least three carbon atoms, such as propylene oxide, butylene oxide (all forms), etc., for example; otherwise the amination does not proceed well. In other words, the hydroxy-terminated polybutadiene that is alkoxylated should, in one embodiment of the invention, not be primary hydroxyl terminated.

The resulting saturated, aminated alkoxylated polymers of this invention may be characterized in one embodiment, by the following formula:

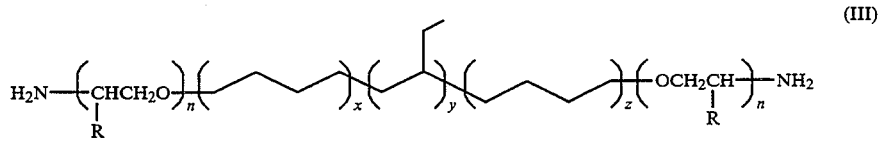
(III)

where R is independently an alkyl group of 1 to 4 carbon atoms;

n independently ranges from about 1 to about 100; and x,y and z are integers and the number average molecular weight of the hydrocarbon backbone is 200 to 5000.

These polyamines are hydrophobic and are useful as curing agents for epoxy resins, and in reaction injection molding (RIM) elastomers. They may also be used in the preparation of flexible polyurethane foams. Essentially all of the double bonds in the original polyol are reduced during the amination step. In addition, a higher degree of amination is achieved using the method of this invention. The process for making the novel materials will be described in more detail below.

The monomer initiator for these primary amine hydrocarbon products should be a homopolymer or copolymer of an unsaturated hydrocarbon. The preferred monomer employed in the method and polyamines of the present invention is butadiene. Other suitable monomers include, but are not limited to isoprene; 1,4-pentadiene; 1,6hexadiene; 1,7-octadiene; styrene; acrylonitrile; methacrylonitrile; α-methylstyrene; methylstyrene; 2,4-dimethylstyrene; ethylstyrene; isopropylstyrene; butylstyrene; substituted styrenes, such as cyanostyrene; phenylstyrene; cyclohexylstyrene; benzylstyrene; nitrostyrene; N,N-dimethylaminostyrene; acetoxystyrene; methyl 4-vinylbenzoate; phenoxystyrene; p-vinyl diphenyl sulfide; p-vinylphenyl phenyl oxide; acrylic and substituted acrylic monomers such as acrylic acid; methacrylic acid; methyl acrylate; 2-hydroxyethyl acrylate; 2-hydroxyethyl methacrylate; methyl methacrylate; cyclohexyl methacrylate; benzyl methacrylate, isopropyl methacrylate; octyl methacrylate; ethyl α-ethoxyacrylate; methyl α-acetoaminoacrylate; butyl acrylate; 2-ethylhexyl acrylate; phenyl acrylate; phenyl methacrylate; N,N-dimethylacrylamide; N,N-dibenzylacrylamide; N-butylacrylamide; methacrylyl formamide; vinyl esters; vinyl ethers; vinyl ketones; vinyl acetate; vinyl alcohol; vinyl butyrate; isopropenyl acetate; vinyl formate; vinyl acrylate; vinyl methacrylate; vinyl methoxy acetate; vinyl benzoate; vinyl toluene; vinyl naphthalene, vinyl methyl ether; vinyl ethyl ether; vinyl propyl ethers; vinyl butyl ethers; vinyl 2-ethylhexyl ether; vinyl phenyl ether;

vinyl 2-methoxyethyl ether; methoxybutadiene; vinyl 2-butoxyethyl ether; 3,4-dihydro-1,2-pyran; 2-butoxy-2'-vinyloxy diethyl ether; vinyl 2-ethylmercaptoethyl ether; vinyl methyl ketone; vinyl ethyl ketone; vinyl phenyl ketone; vinyl ethyl sulfide; vinyl ethyl sulfone; N-methyl-N-vinyl acetamide; N-vinylpyrrolidone; vinyl imidazole; divinyl sulfide; divinyl sulfoxide; divinyl sulfone; sodium vinyl imidazole; divinyl sulfide; divinyl sulfoxide; divinyl sulfone; sodium vinyl sulfonate; methyl vinyl sulfonate; N-vinyl pyrrole; dimethyl fumarate; dimethyl maleate; maleic acid; crotonic acid; fumaric acid; iraconic acid; monomethyl itaconate; t-butylaminoethyl methacrylate; dimethylaminoethyl methacrylate; glycidyl acrylate; allyl alcohol; glycol monoesters of itaconic acid; vinyl pyridine; maleic anhydride; maleimide; N-substituted maleimides, such as N-phenylmaleimide and the like.

The polymerization initiator catalyst may be any suitable initiator for the particular monomers employed. Suitable catalytic initiators useful in producing the polymer compositions of this invention are the free radical type of vinyl polymerization catalysts, such as the peroxides; persulfates; perborates; percarbonates; azo compounds and the like. Specific examples include, but are not limited to hydrogen peroxide; 2,2'-azo-bis-isobutyronitrile (AIBN); dibenzoyl peroxide; lauroyl peroxide; di-t-butyl peroxide; diisopropyl peroxide carbonate; t-butyl peroxy-2-ethylhexanoate; t-butylperneodecanoate; t-butylperbenzoate; t-butyl percrotonate; t-butyl perisobutyrate; di-t-butyl perphthalate; 2,2'-azo-bis-(2-methylbutanenitrile) for example. Other suitable catalysts may be employed, of course.

The polymerization of the monomer, such as butadiene, may be carried out according to conventional, known procedures. The polymers have hydroxyl groups placed on the terminal ends thereof also by any known technique.

The preferred polyamine precursor oligomer employed in the method and polymers of the instant invention is a hydroxyl-terminated polybutadiene oligomer (HTPB) represented by the structure:

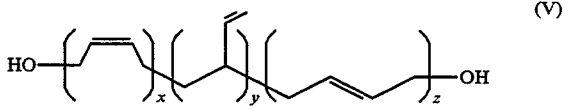

(V)

where x, y and z are integers. These particular hydroxyl-terminated polybutadiene oligomer reactants may be prepared, in one embodiment, according to the methods of U.S. patent applications Ser. Nos. 07/478,292 and 694,590, incorporated by reference herein. The oligomers prepared in those inventions contain hydroxyl groups that are in predominantly primary, terminal positions on the main hydrocarbon chain and are allylic in configuration. Ordinarily, at least about 1.8 hydroxyl groups are present per molecule on the average, and advantageously there are at least from about 2.1 to 3 or more hydroxyls per polymer molecule, often about 2.1 to 2.8. The diene polymer has the majority of its unsaturation in the main hydrocarbon chain, such that x plus z in formula (V) is greater than y. Structure (V) should not be understood as implying that the polymers are necessarily in blocks, but that the cis-1,4; trans-1,4 and vinyl (1,2) unsaturation are usually distributed throughout the polymer molecule. This is true for all such formulae herein. The letter x may represent a number sufficient to give a trans-1,4 unsaturation content of 40–70 percent; y may be a number sufficient to give a 1,2-vinylic unsaturation content to the polymer in the range of about 10–35 percent, while z may be sufficient to provide a cis-1,4-unsaturation of about 10–30 percent, in one embodiment. Often the polymer will contain largely trans-1,4-units, e.g. about 50–65 percent and about 15–25 percent cis-1,4-units, with about 15–25 percent 1,2units. Branching may also occur in the above polymers, especially those prepared at higher temperatures; ether and carbonyl linkages may appear in the lower molecular weight oligomer fractions.

The number average molecular weight of the HTPB oligomers of formula (V) is ordinarily in the range of about 100 to about 20,000, and the hydroxyl (—OH) content of said products is in the range of 0.1 to 20 meq/g, or higher. Preferably, the number average molecular weight is in the range 200–5000 and the hydroxyl content is in the range of 0.05 to 10 meq/g.

These oligomers may be hydroxyl-terminated liquid homopolymers of butadiene with two to twenty moles of an alkylene oxide, such as ethylene oxide, propylene oxide, butylene oxide, or mixtures thereof, added thereto. Alternatively, the intermediates could be hydroxyl-terminated liquid copolymers of butadiene and other vinyl monomers with similar alkylene oxide substituents. As noted previously, it is highly preferred that the materials not be primary hydroxyl-terminated so that the amination may proceed most completely. That the terminating hydroxyl is secondary can be ensured by capping the precursor with an alkylene oxide other than ethylene oxide. With a secondary hydroxyl termination, the final degree of amination may range from 25 to 90% or greater.

In one aspect, it is preferred that the simultaneous hydrogenation and amination be conducted over a catalysts, specifically, a nickel/copper/chromium/molybdenum catalyst. Most preferably, this catalyst contains nickel oxide, copper oxide, chromium oxide and molybdenum oxide, where the nickel oxide is the single greatest component of the active catalyst and the other components are promoters in lesser proportion. In one embodiment, the catalyst has the following proportions: about 10 to about 50 wt. % nickel oxide, about 1 to about 20 wt. % copper oxide, about 0.1 to about 10 wt. % chromium oxide and about 0.1 to about 10 wt. % molybdenum. The catalyst is preferably supported on an inert support, such as an oxide selected from the Group IIIA, IVA or IVB of the Periodic Table. Supports may include alumina, magnesia, silica, zirconia and titania, as well as mixtures thereof. The preferred support is alumina.

Hydrogen and ammonia are preferred as the co-reactants in the last, concurrent step. Hydrogen and ammonia should be used in excess; of at least 10 moles each per every mole of alkoxylated liquid polymer. It is preferred that the molar ratio of hydrogen to alkoxylated liquid polymer be at least 50:1, while the molar ratio of ammonia to alkoxylated liquid polymer be at least 10:1. The alkoxylated liquid polymers are preferably reacted with hydrogen and ammonia simultaneously in the presence of an inert solvent. The solvent should be one which is stable and substantially chemically inert to the components of the reaction system at the reaction temperatures to be employed. Suitable solvents include, but are not limited to, tertiary aliphatic and aromatic alcohols, such as tertiary butanol; 2-methyl-2-butanol; 2- methyl-2-pentanol; triphenylmethanol and the like. The preferred solvent is t-butanol.

Unlike the method of U.S. Pat. No. 4,994,621 where only part of the double bonds are hydrogenated, essentially all of the double bonds are hydrogenated using the method of the present invention. Additionally, the degree of amination using the instant method is also higher than that achieved using the '621 patent method. The present method gives essentially saturated, aminated, alkoxylated polybutadienes with a high degree of amination. By "essentially saturated" is meant at least 90% saturation, preferably at least 96% saturation. By high degree of amination is meant at least 80% amination.

The temperature range for the concurrent hydrogenation and amination procedure may be from about 170° to about 250° C. and the pressure range may be from about 100 to 5000 psi, preferably from about 500 to 4000 psi. The simultaneous hydrogenation and amination may be conducted batchwise, or in a continuous fixed bed or slurry reactor. The products were analyzed by $^1$H and $^{13}$C NMR, chromatography (GPC) and wet chemical techniques.

The resulting saturated polyoxyalkylene polyamines also provide more water-resistant, that is, hydrophobic, epoxy resins than previous polyamines. The invention will be illustrated further with reference to the following non-limiting examples which are presented for increased understanding only.

EXAMPLE 1

Example 1 illustrates the step of synthesizing the alkoxylated hydroxyl-terminated polybutadienes using a tetramethylammonium hydroxide catalyst where starting with a HTPB of about 1390 molecular weight, 80% of the —CH$_2$OH termination has been alkoxylated with propylene oxide to provide secondary hydroxyl termination.

Thirty pounds of Atochem R-20LM (a 1390 molecular weight polybutadiene polyol) and 204 g tetramethylammonium hydroxide pentahydrate were charged into a ten-gallon kettle. The reactor was then purged with prepurified nitrogen. Propylene oxide (4.35 lb) was then reacted at 80°–85° C. at 22 psig over a 0.5 hour period. The reaction mixture was then digested two hours at 80°–85° C. and one hour at 125° C. It was subsequently vacuum stripped to a minimum pressure and purged with nitrogen for 30 minutes. After cooling to 50° C. the product was drained from the kettle. Properties of the finished product were as follows:

| | |
|---|---|
| Total amine, meq/g | 0.019 |
| Hydroxyl no., mg KOH/g | 114 |
| Water, wt. % | 0.01 |
| pH in 10:6 isopropanol/water | 8.5 |
| Viscosity, °F., cs | |
| 77 | 1651 |
| 100 | 763 |

The NMR spectra indicated that 80% of the —CH$_2$OH termination of the Atochem R-20LM had reacted with the propylene oxide, and the olefinic content of the final product was 45.8%.

EXAMPLE 2

Example 2 illustrates concurrent amination and hydrogenation of the polybutadiene polyol of Example 1 achieved using the Ni—Cu—Cr—Mo on alumina catalyst at 200° C. in the presence of an excess ammonia and hydrogen mixture where the initial polybutadiene polyol/ammonia/hydrogen molar ratio is 1:190:285. The resulting product, on analysis showed:

90% amination, by wet chemical analysis.
91% primary amine, by wet chemical analysis.
>80% saturation of the polybutadiene double bonds, by NMR.

Further, this Example illustrates the selective amination of the polybutadiene polyol of Example 1.

To a 550 cc capacity, tubular, continuous reactor system set with temperature; pressure and feed rate controls and operated in the upflow mode, was charged a nickel oxide/chromium oxide/copper oxide/molybdenum oxide catalyst on an alumina support and having a nickel content of about 38 wt. %; 5.5% copper; 0.95% chromium and 0.57% molybdenum. Said catalyst was in extruded form (1/32" diameter). A 50:50 mixture of the polybutadiene polyol of Example 1 plus tertiary butanol solvent was then charged to the reactor system at a rate of 0.1 lb/hr, along with ammonia (0.1 lb/hr) and hydrogen (90 l/hr) such that the molar ratio of polybutadiene polyol to ammonia to hydrogen was approximately 1:190:285. The reactor was then heated to 200° C. and a back pressure of about 2750 psi maintained during hydrogenation/amination of said polyol.

The crude reactor effluent samples A through C were stripped at 100° C. and <5 mm Hg vacuum for 1-2 hours. Typical product had the following properties:

Total acetylatables 1.78 meq/g
Total amine 1.61 meq/g
Primary amine 1.47 meq/g
Melting point 100° C.
Number average mol. wt. (by GPC) 1370
Dispersity 2.4

The NMR spectra of this product indicated that the olefinic content was down to 4.2%. This indicates a product about 96% saturated (91% of available double bonds saturated). This must be contrasted with the highest aminated product described in U.S. Pat. No. 4,994,621 (Example 4) where similar analyses show the residual olefinic content is 14.2% and only 29% of the available double bonds are saturated. Thus, unlike only partial unsaturation achieved in the '621 patent, essential saturation is achieved reliably here, defined as 90% or better saturation. Additionally, the degree of amination achieved in the '621 Example 4 material was on the order of only about 60-62%, while here amination of at least 80% or greater is achievable. More information is given below, in Table I, for the products of Example 2, basis wet chemical, MP, GPC and NMR analyses.

TABLE I

| | | Amination of PO-capped HTPBs | | | | | | |
|---|---|---|---|---|---|---|---|---|
| Ex. | Sample | Total Acetyl. (meq/g) | Total Amine (meq/g) | Primary Amine (meq/g) | MP (°C.) | No. Av. MW (GPC) | Dispersity | Olefin Content (%) (NMR) |
| 1 | | | | | | 1422 | 1.8 | 45.8 |
| 2 | A | 1.71 | 1.24 | | 115 | 1311 | 2.6 | 7.7 |

TABLE I-continued

| | | | | | | | |
|---|---|---|---|---|---|---|---|
| B | 1.62 | 1.41 | | 89 | 1370 | 2.4 | |
| C | 1.78 | 1.61 | 1.47 | 100 | 1321 | 2.4 | 4.2 |

| | ←—Mole % by NMR—→ | | | | | |
|---|---|---|---|---|---|---|
| Sample | Str. (J) | Str. (E) | Str. (D) | Str. (H) | Str. (F) | Str. (K) |
| A | 66 | 24 | Trace | 3 | 2 | 5 |
| C | 85 | 6 | None | 3 | Trace | 6 |

For the most part, $^1$H NMR indicates that structures (A) and (B) have had PO added to them, and then they have been both hydrogenated and the PO-terminal groups aminated (see the diagram, below). The average PO chain length is evidently short (1.5 moles average) as expected. Structure (C), which with uncapped HTPBs has in the past been difficult to aminate (it is usually hydrogenated), appears in these samples to be mostly hydrogenated and aminated. This conclusion is based on the site of the bands believed to be due to structure (K). Some (H) and (L) may have been formed, but so far it has not been possible to distinguish these from structures (E) and (J). The predominant products have structure (J).

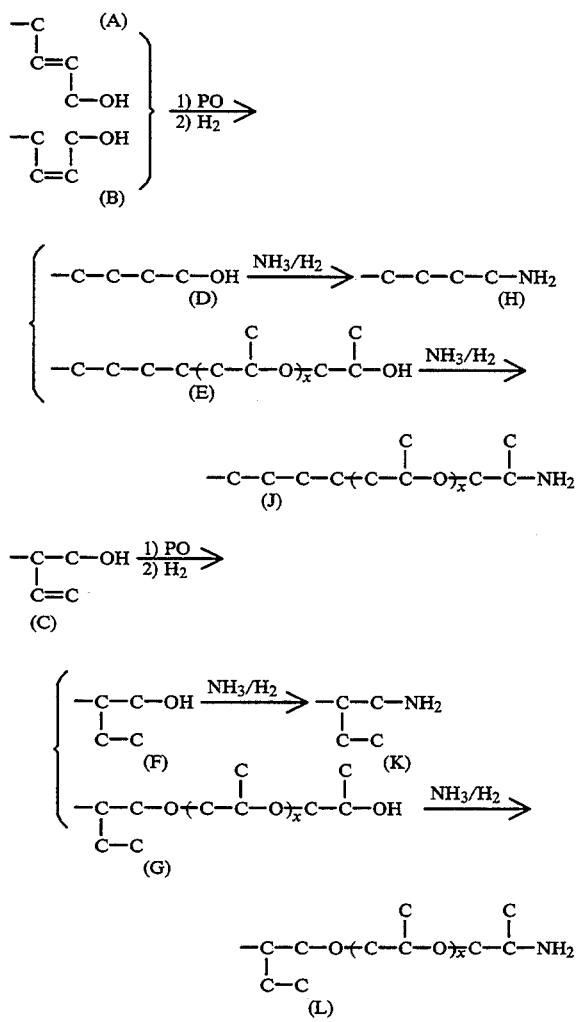

The major reaction paths during the amination portion of the concurrent hydrogenation/amination of alkylene oxide capped HTPBs may be summarized above.

EXAMPLE 3

This Example illustrates the use of the saturated polyamine products of Example 2 in the preparation of a flexible, polyurethane foam. Formulation, details of preparation and foam properties are shown below:

| Formulation | |
|---|---|
| Poly G 32-48 | 100 |
| Goldschmidt B-8231 | 1.3 |
| Water | 5.1 |
| MeCl$_2$ | 5.0 |
| Firemaster 642 | 9.0 |
| Dabco T-10 | 0.5 |
| Saturated polyamine from Ex. 2 | 10.0 |
| Toluene diisocyanate | 63.55 |
| Preparation | |
| Cream time, sec. | 10 |
| Rise time, sec. | 136 |
| Post cure, °C. (hr) | 100 (1) |
| Property | |
| Density, pcf | 1.40 |

EXAMPLES 4–14

Following the procedure of Example 2, amination of PO-capped HTPBs has been demonstrated over a wide range of experimental conditions using the same 550 cc capacity unit and the Ni—Cu—Cr—Mo on alumina catalyst. A summary of the results, particularly the wet chemical, GPC and $^1$H NMR data for each individual product, may be found in the accompanying Tables II and III. The operating parameters varied during this study included:

a) Polyol feed rate (1:1 with t-butanol, total rates 0.05–0.5 lb/hr).
b) Ammonia feed rate (0.02–0.5 lb/hr).
c) Hydrogen feed rate (5–300 l/hr).
d) Operating temperature (185°–215° C).

All aminated products, after work-up, were solids—indicating extensive hydrogenation of the HTPB olefinic backbone. The highest functionality (1.90 meq/g acetylatables) was achieved at moderate hydrogen feed rates (30 l/hr, Example 11). In this case, the amination level was 82% and the primary amine content 94%, Example 10 was achieved at the lowest polyol feed rate. However, the low total acetylatables value for this sample (1.67 meq/g) indicates some loss of end-group functionality under these conditions. Not surprisingly, the highest level of unsaturation (18.4%) was realized at the lowest hydrogen feed rate (Example 12). However in this case, the product amine level was only 1.10 meq/g, although the estimated primary amine value was 96%.

Degradation of the Ni—Cu—Cr—Mo catalyst, indicated by gray fines in the product efficient, appeared to be a problem only at the highest feed rates (e.g. in Example 7). Surprisingly, total amine and primary amine values (1.22 and 1.13 for Ex. 7) were depressed under those conditions.

EXAMPLE 15

Following the procedures of Example 2, a twenty-mole PO adduct of Atochem R-20LM polyol, having a hydroxyl number of 64 mg KOH/g was aminated also under standard conditions with a fresh charge of the Ni—Cu—Cr—Mo on alumina (1/32" extruded) catalyst. Product analyses for Samples A through L, summarized in Tables IV and V, show typically about 82% amination levels with 96% primary amine content and 3.4% residual olefin (e.g. Sample D). The $^1$H NMR data also indicate 85–89 mole percent secondary alkyl primary amine termination for these crude, stripped, products (see Table V). While the amination level in Tables IV and V is a little lower than that reported for the 5 molar PO adducts in Table I, the product series in Tables IV and V is noteworthy in that their NMR spectra do not exhibit measurable primary alkyl, primary amine functionality that would be indicative of uncapped hydroxyl end groups in the Example 15 feedstock (see the diagram of the major reactor paths, above).

TABLE II

Amination of PO-capped HTPBs

| Ex. | Polyol feed | Polyol + tBA (lb/hr) | NH$_3$ (lb/hr) | H$_2$ (l/hr) | Operating Temp. °C. | MP, °C. | Total Acetyl, meq/g | Total Amine, meq/g | Primary Amine, meq/g | # Ave. MW | Disp. | Product Appearance |
|---|---|---|---|---|---|---|---|---|---|---|---|---|
| 4 | 1 | 0.1 | 0.1 | 90 | 200 | 90 | 1.80 | 1.53 | 1.42 | 1324 | 2.4 | Yellow solid |
| 5 | " | 0.1 | 0.1 | 90 | 185 | 84 | 1.83 | 1.55 | 1.50 | 1335 | 2.3 | Yellow solid |
| 6 | " | 0.1 | 0.1 | 90 | 215 | 95 | 1.79 | 1.55 | 1.47 | 1355 | 2.3 | Yellow solid |
| 7 | " | 0.1 | 0.5 | 90 | 200 | 90 | 1.88 | 1.22 | 1.13 | 1276 | 2.4 | Gray solid |
| 8 | 2 | 0.1 | 0.02 | 90 | 200 | 100 | 1.71 | 1.46 | 1.34 | 1568 | 2.1 | Yellow green solid |
| 9 | " | 0.5 | 0.1 | 90 | 200 | 85 | N.D. | 1.35 | 1.29 | 1027 | 3.0 | Yellow orange solid |
| 10 | " | 0.05 | 0.1 | 90 | 200 | 80 | 1.67 | 1.61 | 1.51 | 953 | 3.4 | Yellow solid |
| 11 | " | 0.1 | 0.1 | 30 | 200 | 80 | 1.90 | 1.55 | 1.45 | 874 | 3.7 | Yellow solid |
| 12 | " | 0.1 | 0.1 | 5 | 200 | 88 | N.D. | 1.10 | 1.06 | 1197 | 2.6 | Yellow orange solid |
| 13 | " | 0.1 | 0.1 | 300 | 200 | 88 | 1.76 | 1.04 | 0.88 | 1221 | 3.1 | Yellow solid |
| 14 | " | 0.1 | 0.5 | 90 | 200 | 90 | 1.85 | 1.48 | 1.39 | 1054 | 5.2 | Yellow orange solid |

1 A PO-capped HTPB (R-20LM) having a OH no. of 114 mg KOH/g.
2 A PO-capped HTPB (R-20LM) having a OH no. of 118 mg KOH/g.

TABLE III

Amination of PO-capped HTPBs

| Ex. | Polyol + tBa (lb/hr) | NH$_3$ (lb/hr) | H$_2$ (l/hr) | Temp. °C. | —CCNH$_2$ (C\|) | —CCOH (C\|) | —CCCCNH$_2$ | —C—COH (C—C\|) | —C—CNH$_2$ (C—C\|) | % Olefin v. Total C |
|---|---|---|---|---|---|---|---|---|---|---|
| 4 | 0.1 | 0.1 | 90 | 200 | 76 | 7 | 8 | 1 | 8 | 5.2 |
| 5 | 0.1 | 0.1 | 90 | 185 | 77 | 11 | 4 | 1 | 6 | 5.3 |
| 6 | 0.1 | 0.1 | 90 | 215 | | | | | | |
| 7 | 0.1 | 0.5 | 90 | 200 | 79 | 9 | 6 | <1 | 6 | 5.4 |
| 8 | 0.1 | 0.02 | 90 | 200 | | | | | | |
| 9 | 0.5 | 0.1 | 90 | 200 | 65 | 22 | 4 | 2 | 6 | 11.1 |
| 10 | 0.05 | 0.1 | 90 | 200 | 80 | 7 | 5 | <1 | 7 | 4.4 |
| 11 | 0.1 | 0.1 | 30 | 200 | 76 | 7 | 8 | 1 | 8 | 6.2 |
| 12 | 0.1 | 0.1 | 5 | 200 | 62 | 28 | 4 | 3 | 3 | 18.4 |
| 13 | 0.1 | 0.1 | 300 | 200 | 72 | 17 | 3 | 2 | 5 | 8.2 |
| 14 | 0.1 | 0.5 | 90 | 200 | 72 | 11 | 8 | 1 | 8 | 8.7 |

TABLE IV

Amination of PO-capped HTPBs[3]

| Ex. | Operating Temp. °C. | Sample | Total Acetyl, meq/g | Total Amine, meq/g | Primary Amine, meq/g | MP, °C. | # Ave. MW(GPC) | Disp. | Olefin Content (%) by NMR |
|---|---|---|---|---|---|---|---|---|---|
| 15 | 200 | | 1.33 | | | | 1889 | 1.8 | |
| | 200 | A | 1.29 | 1.05 | 1.01 | 95 | 1823 | 2.3 | 2.7 |
| | 200 | B | — | 1.05 | 1.00 | 75 | 1727 | 2.3 | 3.4 |
| | 200 | C | 1.3 | 1.05 | 0.99 | 75 | 1802 | 2.3 | 3.0 |
| | 200 | D | 1.3 | 1.07 | 1.03 | 119 | 1750 | 2.3 | 3.4 |
| | 200 | E | 1.5 | 1.06 | 1.02 | 76 | 1481 | 2.7 | 3.4 |
| | 200 | F | 1.34 | 1.05 | 1.02 | 116 | 1736 | 2.4 | 3.8 |
| | 200 | G | 1.21 | 1.06 | 1.01 | 80 | 1751 | 2.4 | 3.4 |
| | 200 | H | 1.14 | 1.06 | 1.00 | 115 | 1709 | 2.4 | 3.1 |
| | 200 | I | 1.39 | 1.06 | 1.03 | 77 | 1733 | 2.5 | 4.2 |
| | 200 | J | 1.29 | 1.05 | 1.01 | 110 | 1740 | 2.4 | 3.9 |
| | 200 | K | 1.37 | 1.03 | 0.99 | 115 | 1795 | 2.4 | 3.3 |
| | 200 | L | 1.21 | 1.04 | 1.00 | 120 | 1735 | 2.5 | 4.1 |

[3] In all instances the polyol feed was a PO-capped HTPB (R-20LM) having OH no. of 64 KOH/g.

TABLE V

Amination of PO-capped HTPBs
Product Amine
NMR Relative Mole % Termination

| Ex. | Sample | $\overset{C}{\underset{|}{-OCCNH_2}}$ | $\overset{C}{\underset{|}{-OCCOH}}$ | $-CCCCOH$ | $-CCCCNH_2$ | $\underset{-C-COH}{\overset{C-C}{|}}$ | $\underset{-C-CNH_2}{\overset{C-C}{|}}$ |
|---|---|---|---|---|---|---|---|
| 15 | A | 87 | 10 | None | <1 | 3 | None |
|    | B | 86 | 11 | None | <1 | 2 | None |
|    | C | 87 | 10 | None | <1 | 3 | None |
|    | D | 88 | 9  | None | <1 | 2 | None |
|    | E | 87 | 10 | None | <1 | 2 | None |
|    | F | 87 | 11 | None | <1 | 2 | None |
|    | G | 87 | 10 | None | <1 | 2 | None |
|    | H | 89 | 8  | None | <1 | 2 | None |
|    | I | 85 | 13 | None | <1 | 2 | None |
|    | J | 86 | 11 | None | <1 | 2 | None |
|    | K | 85 | 12 | None | <1 | 2 | None |
|    | L | 87 | 11 | None | <1 | 2 | None |

Many modifications may be made in the process of this invention without departing from the spirit and scope thereof which are defined only in the appended claims. For example, one skilled in the art may discover that particular compounds or proportions thereof, which may not be explicitly recited herein, but which are nevertheless anticipated, would give desirable results. A certain combination of reaction temperatures, reactant proportions, etc. may be found to have particular advantages.

GLOSSARY

| | |
|---|---|
| Dabco T-10 | 50% stannous octoate in dioctyl phthalate; tin catalyst made by M&T Chemicals. |
| Firemaster 642 | A halogenated phosphate fire retardant made by Great Lakes Chemical. |
| Goldschmidt B-8231 | A silicone oil surfactant made by Goldschmidt. |
| Poly G 32-48 | A 3500 molecular weight glycerin triol having about 10% internal ethylene oxide made by Olin Chemicals. |
| tBA | tertiary butanol |

We claim:

1. A process for making saturated, aminated alkoxylated polymers comprising the steps of:
   (1) polymerizing one or more unsaturated hydrocarbons to form a liquid polymer, where at least one of the unsaturated hydrocarbons is butadiene;
   (2) providing the liquid polymer with terminal hydroxyl groups to give a hydroxyl-terminated polybutadiene (HTPB);
   (3) alkoxylating the HTPB with one or more alkylene oxides having at least three carbon atoms to provide secondary terminal hydroxyl groups;
   (4) simultaneously aminating and hydrogenating the alkoxylated liquid polymer to produce an essentially completely saturated, essentially completely aminated, alkoxylated liquid polymer in the presence of hydrogen and ammonia and a catalyst consisting of components nickel oxide, copper oxide, chromium oxide and molybdenum oxide, and where the molar ratio of hydrogen to ammonia to secondary hydroxyl groups on the alkoxylated liquid polymer is in the range of about at least 50 to at least 10 to 1.

2. The process of claim 1 where the alkylene oxide of step (3) is selected from the group consisting of propylene oxide, butylene oxide and mixtures thereof.

3. The process of claim 1 where the catalyst of step (4) is supported on an oxide selected from the group consisting of alumina, silica, zirconia, magnesia and titania, as well as mixtures thereof.

4. The process of claim 1 where the catalyst has the following proportions: about 10 to about 50 wt. % nickel oxide, about 1 to about 20 wt. % copper oxide, about 0.1 to about 10 wt. % chromium oxide and about 0.1 to about 10 wt. % molybdenum oxide.

5. The process of claim 1 where the step (4) of simultaneous aminating and hydrogenating is conducted at a molar ratio of hydrogen to ammonia to alkoxylated HTPB in the range of about at least 50 to at least 10 to 1.

6. The process of claim 1 where the step (4) of simultaneous aminating and hydrogenating is conducted in the temperature range from about 170° C. to about 250° C.

7. The process of claim 1 where the step (4) of simultaneous aminating and hydrogenating is conducted in the pressure range of from about 100 psi to about 5000 psi.

8. The process of claim 1 where the step (4) of simultaneous aminating and hydrogenating is conducted in the presence of t-butanol as an inert solvent.

9. A process for making saturated, aminated alkoxylated polymers comprising the steps of:
   (1) polymerizing one or more unsaturated hydrocarbons to form a liquid polymer, where at least one of the unsaturated hydrocarbons is butadiene;
   (2) providing the liquid polymer with terminal hydroxyl groups to give a hydroxyl-terminated polybutadiene (HTPB);
   (3) alkoxylating the HTPB with one or more alkylene oxides having at least three carbon atoms to provide secondary terminal hydroxyl groups;
   (4) simultaneously aminating and hydrogenating the alkoxylated liquid polymer to produce an essentially completely saturated, essentially completely aminated, alkoxylated liquid polymer in the presence of
   hydrogen and
   ammonia and
   a catalyst consisting of:
      about 10 to about 50 wt. % nickel oxide,
      about 1 to about 20 wt. % copper oxide,
      about 0.1 to about 10 wt. % chromium oxide, and
      about 0.1 to about 10 wt. % molybdenum oxide, and where the molar ratio of hydrogen to ammonia to secondary hydroxyl groups on the alkoxylated liquid polymer is in the range of at least 50 to at least 10 to 1, and where the aminating and hydrogenating are conducted at a temperature in the range from about 170 to about 250° C. and at a pressure in the range of from about 100 psi to about 5000 psi.

10. The process of claim 9 where the alkylene oxide of step (3) is selected from the group consisting of propylene oxide, butylene oxide and mixtures thereof.

11. The process of claim 9 where the catalyst of step (4) is supported on an oxide selected from the group consisting of alumina, silica, zirconia, magnesia and titania, as well as mixtures thereof.

12. The process of claim 9 where the step (4) of simultaneous aminating and hydrogenating is conducted at a molar ratio of hydrogen to ammonia to alkoxylated HTPB in the range of about at least 50 to about at least 10 to 1.

13. The process of claim 9 where the step (4) of simultaneous aminating and hydrogenating is conducted in the presence of t-butanol as an inert solvent.

* * * * *